United States Patent
Mizuno et al.

[11] Patent Number: 5,750,990
[45] Date of Patent: May 12, 1998

[54] METHOD FOR MEASURING CRITICAL DIMENSION OF PATTERN ON SAMPLE

[75] Inventors: Fumio Mizuno, Tokorozawa; Osamu Satoh, Hitachinaka, both of Japan

[73] Assignee: Hitachi, Ltd., Tokyo, Japan

[21] Appl. No.: 771,325

[22] Filed: Dec. 20, 1996

[30] Foreign Application Priority Data

Dec. 28, 1995 [JP] Japan ................ 7-342932

[51] Int. Cl.$^6$ .................................. H01J 37/28
[52] U.S. Cl. ...................................... 250/307
[58] Field of Search .......................... 250/307, 306, 250/310, 311; 73/105; 324/149; 356/355, 357, 359

[56] References Cited

U.S. PATENT DOCUMENTS 5,434,409  7/1995  Tsubusaki ................ 250/307
5,644,512  7/1997  Chernoff et al. ........... 250/307

Primary Examiner—Kiet T. Nguyen
Attorney, Agent, or Firm—Kenyon & Kenyon

[57] ABSTRACT

In a pattern dimension measuring method for scanning a sample at a predetermined scanning pitch by a scanning probe as in a scanning electron microscope, forming a sample image using a scanning signal obtained from the sample, scanning a predetermined portion of a pattern to be measured in a sample image by said probe, and measuring a dimension of said predetermined portion by processing obtained scanning signal according to a predetermined algorithm, said scanning pitch is varied according to the case for positioning the pattern to be measured and the case for measuring the pattern dimension when observing in a low magnification, and said scanning pitch for measuring the pattern dimension is adjusted to be small, about a diameter of the probe.

10 Claims, 9 Drawing Sheets

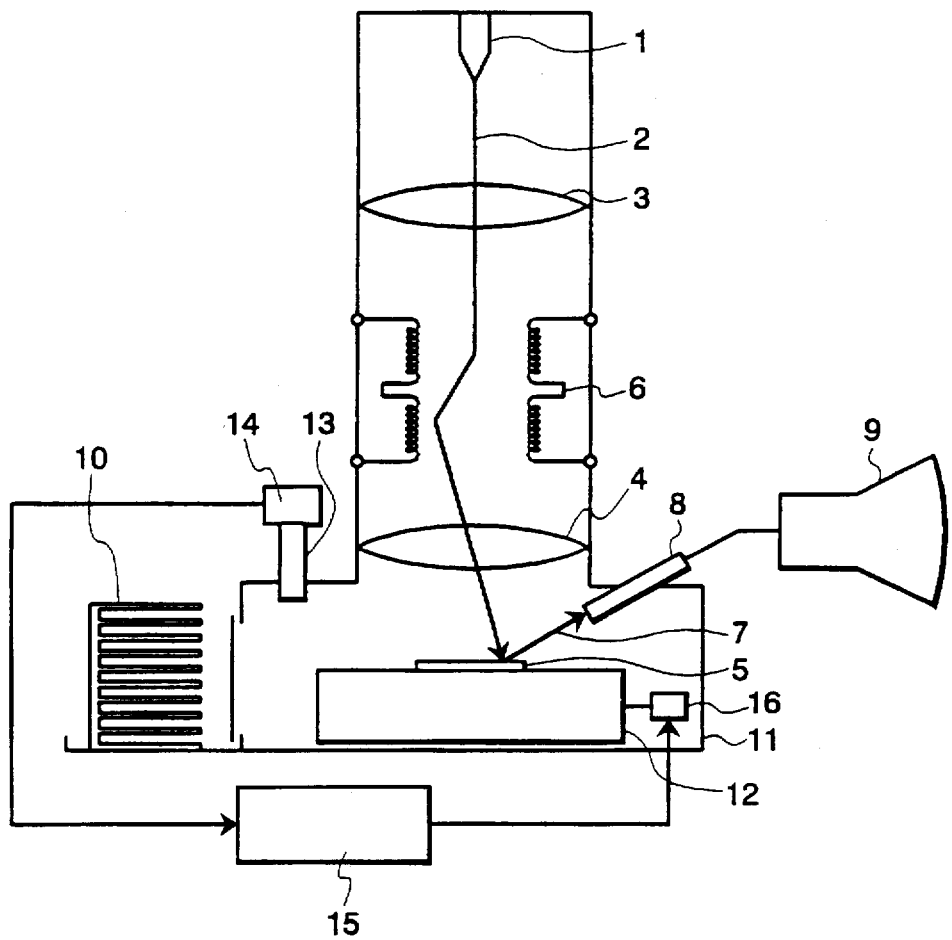
FIG. 1 *PRIOR ART*

FIG. 2A  PRIOR ART
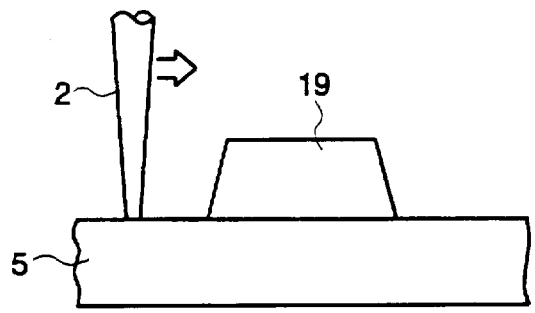
FIG. 2B  PRIOR ART
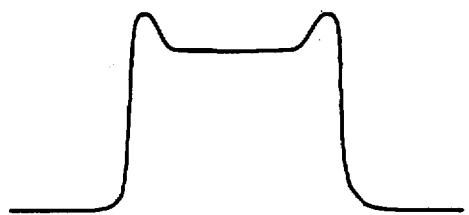
PRIOR ART　　PRIOR ART　　PRIOR ART
FIG. 2C　　FIG. 2D　　FIG. 2E
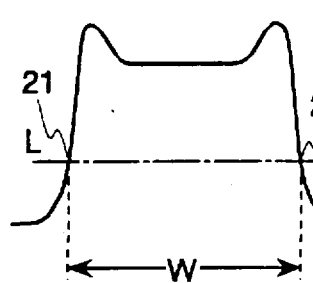 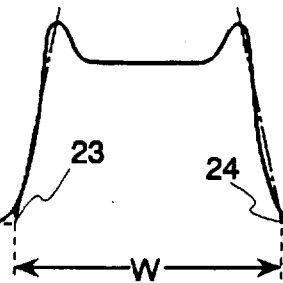 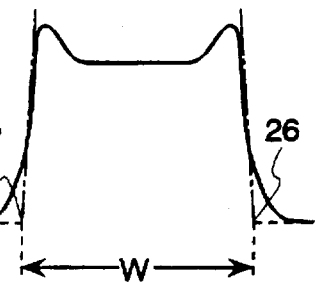
THRESHOLD METHOD　　LINEAR APPROXIMATION METHOD　　MAXIMUM SLOPE METHOD

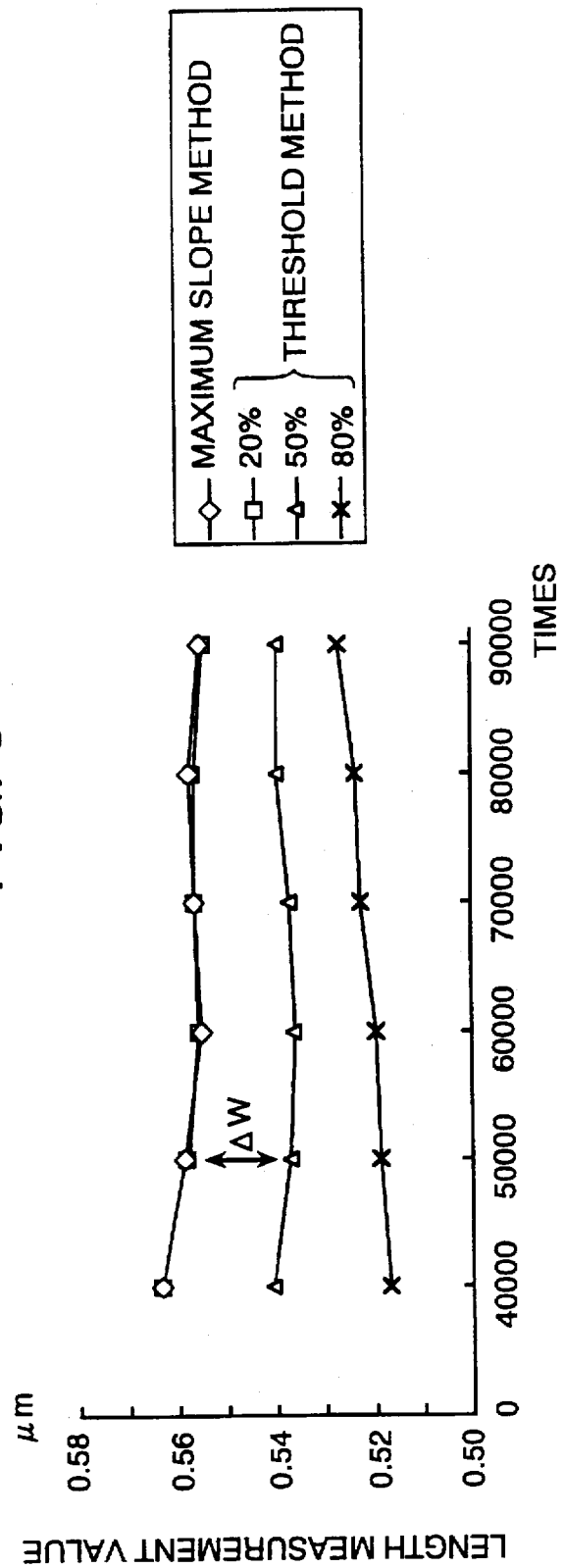

W = W1 − ΔW

METHOD FOR MEASURING CRITICAL DIMENSION OF PATTERN ON SAMPLE

BACKGROUND OF THE INVENTION

The present invention relates to a method for measuring a pattern dimension employing a scanning probe, such as a scanning electron microscope.

Measurement of a fine pattern dimension employing a probe of particle beam, such as an electron beam, an ion beam, optical beam and so forth, or a mechanical probe, has been performed.

As a typical example, discussion will be given for the case where a critical dimension measurement of a pattern processed in a semiconductor manufacturing process is performed employing a scanning electron microscope (length measuring SEM).

FIG. 1 is a schematic illustration showing basic principle and construction of the length measurement SEM. An electron beam 2 discharged from an electron gun 1 is converged through a condenser lens 3 and an objective lens 4 and focused on a wafer 5. Simultaneously, the electron beam 2 is deflected its path by means of a deflector 6 for performing two-dimensional or linear scan on the wafer 5. From the wafer portion irradiated by the electron beam 2, a secondary electron 7 is discharged. The secondary electron 7 is detected by a secondary electron detector 8, converted into an electrical signal, and then subject to processes, such as amplification or so forth.

A secondary electron signal is used as a brilliance modulation signal or a deflection signal of a display 9, such as CRT or so forth. In synchronism with two-dimensional scan on the wafer surface by the electron beam 2, a screen of the display 9 is two-dimensionally scanned to modulate luminance signal with the secondary electron signal. Thus, a SEM image is formed on the display 9. On the other hand, with taking a scanning signal of the electron beam 2 as a X deflection signal of the display 9 and taking a secondary electron detection signal as Y deflection signal of the display, a line profile can be displayed on the display.

One example of a procedure in measurement of a pattern dimension on the wafer employing the length measuring SEM will be discussed hereinafter. The wafer 5 to be taken out from a wafer carrier 10 is previously aligned with reference to an orientation flat or a notch. In conjunction therewith, a wafer number written on the wafer is read by a wafer number reader (not shown). The wafer number is unique to each wafer. With taking the read out wafer number as key, a recipe corresponding to the wafer 5 to be measured can be read out. The recipe defines a measurement procedure of the wafer or measurement condition and is registered per each wafer. All of subsequent operations are performed according to this recipe.

After reading out of the wafer number, the wafer 5 is fed into a sample chamber 11 held in vacuum condition and loaded on a XY stage 12. The wafer 5 loaded on the XY stage 12 is aligned employing an alignment pattern formed on the latter. The alignment pattern is picked-up with a magnification in the extent of several hundreds employing an optical microscope 13 and an image pick-up device 14 installed on an upper wall of the sample chamber 11. The picked-up alignment pattern is compared with a preliminarily registered reference image by a control unit 15. The control unit 15 places the wafer in alignment by correcting position coordinates of the XY stage 12 by driving a driving motor 16 so that the picked-up pattern is just overlapped with the reference image.

After alignment, the wafer 5 to be measured is shifted to a predetermined length measurement point with the stage. At the length measurement point, the scanning electron beam 2 is irradiated to form the SEM image of high magnification. Employing this SEM image, high precision positioning of the pattern to be measured is formed on the wafer. Similarly to alignment operation, positioning is performed by comparing the SEM image at the measuring point with the reference image and effecting fine adjustment of the electron beam scanning region so that the SEM image is exactly overlapped with the reference image. The positioned wafer 5 is positioned to place the pattern to be measured, at substantially center of the screen, namely just below the electron beam 2. At this condition, the electron beam 2 performs linear scan on the pattern to be measured with the same scanning pitch (pixel size) to that upon formation of the SEM image. From obtained line profile, the pattern dimension is obtained according to a predetermined length measurement algorithm. When a plurality of measurement points are present on the wafer, operation subsequent to shifting of the length measurement point may be repeated. On the other hand, when a plurality of wafers to be measured are present in the wafer carrier, the operation subsequent to the transfer of the wafer into the sample chamber 11 may be repeated.

While there are various length measuring algorithms for obtaining the pattern dimension from the line profile, a threshold method shown in FIG. 2, a maximum slop method, a linear approximation method and so forth may be typically employed. In FIG. 2, (a) diagrammatically shows manner of scanning the pattern 19 to be measured on the wafer 5 by the electron beam 2, (b) shows the obtained line profile. On the other hand, (c) is an explanatory illustration for explaining the threshold method, (d) is an explanatory illustration for explaining the linear approximation method and (e) is an explanatory illustration for explaining the maximum slop method, respectively.

The threshold is a method to obtain positions 21 and 22 where slope portions at both ends of the line profile intersect with a predetermined level (threshold value) L, and to take a distance W between the two positions 21 and 22 as the dimension of the pattern 19. The threshold value L is normally determined as a ratio relative to the maximum height of the line profile. The line approximation method is a method to linearly approximate the sloped portions at both ends of the line profile by least-squares method and to take a distance W between intersecting points 23 and 24 between respective straight lines and a base line as the pattern dimension. On the other hand, the maximum slop method is a method to set tangent lines at portions where the sloped portions at both ends of the line profile have maximum inclination and to take distance W between intersections 25 and 26 between the tangent lines and the base line as the pattern dimension.

Upon positioning of the pattern to be measured, for facilitating finding of a desired pattern among a plurality of patterns, the SEM image of relatively low magnification are frequently employed. On the other hand, upon measurement of the pattern dimension of high magnification, measurement can be performed by varying magnification.

On the hand, even when the same pattern is measured, there is a phenomenon to cause variation of the measured value and the measurement precision depending upon magnification, if magnification is varied. Therefore, when measurement at low magnification is performed for the purpose as set forth above, the measured value may significantly differentiated from a real dimension, and significant fluctuation of the measured value is increased. On the other hand, the linear approximation method and the maximum slop method have large dependency of measurement magnification of the measured value in comparison with the threshold method.

SUMMARY OF THE INVENTION

The present invention is worked out in view of the problem in such prior art. It is an object to provide a method which can accurately obtain pattern dimension irrespective of setting of measurement magnification or length measuring algorithm derived the pattern dimension from the line profile.

FIG. 3 is an example of measurement of dependence of SEM image magnification of the measured value, and FIG. 4 shows a magnification dependence of fluctuation (3σ) of the measured value. In the drawings, the measured values in the maximum slope method and the measured value in the threshold method are shown. Indication of 20%, 50% and 80% in the threshold method represents the threshold level. For example, the graph indicated as 20% represents the result of measurement in the case where the threshold level in the threshold method is set at 20% of the maximum height of the line profile.

From FIGS. 3 and 4, it is appreciated that when the threshold level in the maximum slop method and the threshold method is set at 20%, the measured value of the pattern width becomes large in relatively low magnification, and measurement fluctuation is increased. On the other hand, in the threshold method with setting the threshold level at 80%, the measured value of the pattern width becomes large as measured at high magnification.

As a result of study for the cause of measurement magnification dependency of the measured value of the pattern dimension, it is appreciated that the measurement magnification becomes small to make the scanning pitch (pixel size) large and rounding of the waveform of the line profile is increased. Particularly, this tendency becomes remarkable when the scanning pitch is greater than or equal to the diameter of the electron beam.

FIG. 5 diagrammatically shows this mechanism. White circles shown at the scanning pitch represent sampling points by the electron beam 2. A pixel size d is equal to a range covered by one sampling point. Drawn as the line profile is the line profile created by data sampled at the scanning pitch. Figures written as magnification is for reference. As shown in (a), rounding of the waveform of the line profile becomes large at low magnification, and the size W of the pattern appearing on the line profile becomes greater than an actual pattern 19. According to increasing of magnification in order of (b), (c) and (d), the sizes W of the patterns appearing on the line profile are varied.

The present invention is worked out on the basis of breakthrough of cause of measurement magnification dependency of the measured value of the pattern dimension. A pattern dimension measurement method for deriving a dimension of a predetermined portion by scanning the sample at a predetermined pitch by a probe, forming a sample image using a scanning signal obtained from the sample, and processing the obtained scanning signal by a predetermined length measurement algorithm, is characterized by varying the scanning pitch between that upon formation of the sample image and that upon measurement of the pattern dimension. It is preferred that the scanning pitch upon obtaining the pattern dimension is in the extent of an electron beam diameter.

Also, the present invention is characterized by setting of the threshold value in the low magnification region at approximately 50%, in the pattern dimension measuring method to obtain the dimension at the predetermined position by processing the obtained scanning signal in the threshold method.

Furthermore, the present invention is characterized by taking a value derived by subtracting a predetermined value determined depending upon the measurement magnification from a dimension value obtained in the linear approximation method or the maximum slop method.

Also, the present invention uses an algorithm to derive the dimension by the threshold method after drawing the linear approximation line or maximum slop line, as the length measurement algorithm.

According to the present invention, since the measurement magnification dependency of the dimension measured value is decreased, it becomes possible to obtain the measured value close to the actual dimension even in measurement at low magnification, and to enable measurement with high precision of reproductivity.

BRIEF DESCRIPTION OF THE DRAWINGS

FIG. 1 shows a schematic view for explaining principle and construction of a SEM.

FIG. 2A shows a schematic view for showing a scanning electron beam on a pattern to be measured on a wafer.

FIG. 2B show a schematic view of a line profile obtained by scanning with the electron beam.

FIG. 2C show an explanatory view for obtaining a pattern dimension using a threshold value method.

FIG. 2D show an explanatory view for obtaining a pattern dimension using a linear approximation method.

FIG. 2E show an explanatory view for obtaining a pattern dimension using a maximum slope method.

FIG. 3 is a schematic view for showing an example of magnification dependence of a length measurement value.

DETAILED DESCRIPTION OF THE PREFERRED EMBODIMENTS

Discussion will be given hereinafter for a mode for implementing the present invention with reference to the drawings. Here, discussion will be given in terms of the case where a dimension of a pattern on a wafer is measured by employing a length measuring SEM.

Figure 6:
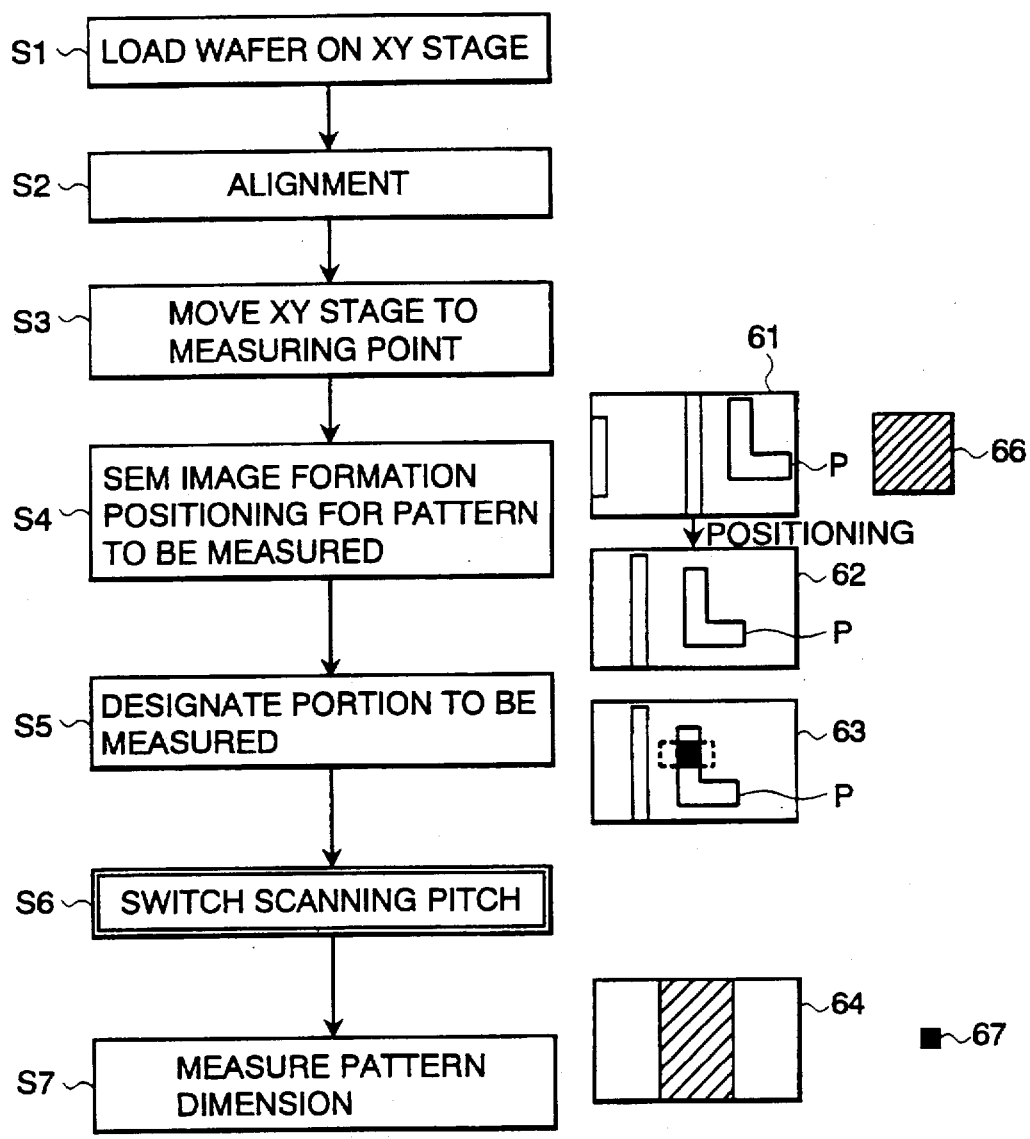
FIG. 6 is a schematic view of a pattern dimension measuring method in the present invention.

FIG. 6 is an explanatory illustration of the first embodiment. In this embodiment, upon measurement at low magnification, scanning pitch upon positioning of a pattern to be measured and scanning pitch upon obtaining a pattern dimension are automatically switched to make the scanning pitch upon obtaining the pattern dimension small in the extent of a diameter of the electron beam.

Observation and measurement are performed in accordance with a shown operational flowchart. At first, a wafer to be measured is loaded on a XY stage (S1), and wafer alignment is performed using an alignment pattern on the wafer (S2). Subsequently, the XY stage is moved to a length measuring point (S3), and positioning of the pattern to be measured is performed using a specific pattern among SEM images 61 so that the pattern p to be measured is located just below the electron beam (S4). In a SEM image 62 at a timing where positioning of the pattern p to be measured is completed, the pattern p to be measured is located at the center of a screen. Subsequently, as surrounded by broken line in a SEM image 63, a portion to be measured in the pattern p is designated (S5).

When step S5 is completed, the scanning pitch is automatically switched to be substantially equal to the electron beam diameter (S6), and then, measurement of the pattern dimension is performed with this small pitch (S7). At this time, a scanning region of the electron beam becomes as represented by 64. Representing a relative dimension of a pixel of he SEM image upon positioning at step S4 by 66, a pixel dimension of the SEM image upon pattern dimension measurement is represented by 67.

As set forth above, irrespective of magnification of observation upon positioning of the pattern to be measured, dimension measurement can be constantly performed with the same precision by switching the scanning pitch upon pattern dimension measurement to a predetermined pitch adapted for accurately measuring an actual dimension of the pattern, and thus fluctuation of the length measurement value due to difference of magnification can be avoided.

FIG. 7 is an explanatory illustration of the second embodiment. In this embodiment, upon measurement in threshold method at low magnification, a threshold value is automatically set at a level of approximately 50%.

Figure 7A:
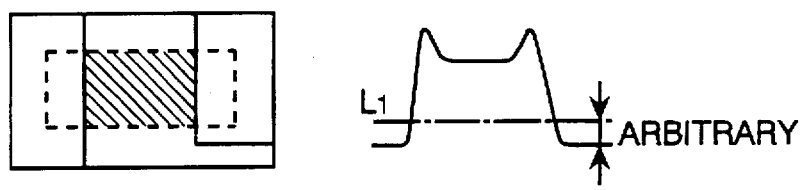
FIG. 7A shows an explanatory view for measuring the pattern dimension in a high magnification by the threshold value method.

FIG. 7(a) is an illustration for explaining pattern dimension measurement in the threshold method at high magnification. Pattern dimension measurement is performed in a region surrounded by broken line designated among SEM image shown in left, and then the line profile is shown in right. In case of high magnification, as can be appreciated from FIG. 3, since magnification dependency of the length measurement value is small, fluctuation of the length measurement value due to magnification is small even if the threshold level L1 is set arbitrarily.

Figure 7B:
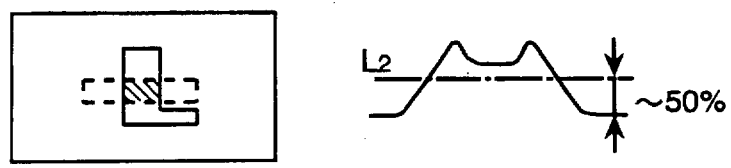
FIG. 7B shows an explanatory view for measuring the pattern dimension in a low magnification by the threshold value method.

However, in case of low magnification, as can be appreciated from FIG. 3, fluctuation of the length measurement value depending upon magnification is large at the threshold value of 20% and 80%. However, at the threshold value of 50%, fluctuation of the length measurement value depending upon magnification is small. Accordingly, as shown in FIG. 7(b), when measurement is performed in threshold method at low magnification, fluctuation of the length measurement value depending upon magnification can be suppressed to be minimum by automatically setting a threshold value L2 at about 50%.

Figure 8:
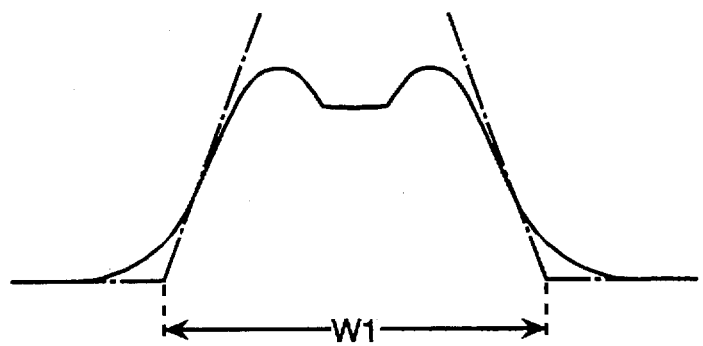
FIG. 8 is an explanatory view for measuring the pattern dimension based on a predetermined value determined according to a pattern dimension measuring value and observing magnification in the low magnification by the maximum slope method.

FIG. 8 is an explanatory illustration of the third embodiment. In this embodiment, upon measurement in the linear approximation method or the maximum slope method, the measured value is corrected to a value derived by subtracting a predetermined value depending upon magnification of observation from the value derived with the linear approximation line or the maximum slope line.

FIG. 8 is an example of the maximum slope method. When the magnification is fifty thousands times and when the pattern dimension obtained from the line profile by the maximum slope method is W1, the pattern dimension W is calculated and displayed by the following equation.

$$W = W1 - \Delta W$$

Here, $\Delta W$ is a difference between the length measurement value in the maximum slope method at the magnification of fifty thousands times and the length measurement value at the threshold value of approximately 50%. As set forth above, since the fluctuation of the length measurement value in the threshold method at the threshold value of 50% is small, at low magnification, the length measurement value not depending upon the magnification can be obtained by converting the measured value in the maximum slope method into the length measurement value in the threshold method at the threshold value of about 50%. As can be clear from FIG. 3, since $\Delta W$ has magnification dependence, by preliminarily deriving and storing the values of $\Delta W$ per respective magnifications, the value of $\Delta W$ corresponding to the magnification is used in the foregoing calculation.

Here, discussion has been given with respect to the maximum slope method. Even in the linear approximation method, by converting into the length measurement value into the length measurement value to be derived in the threshold method with the threshold value of 50%, magnification dependence of the length measurement value at low magnification can be avoided.

Figure 4:
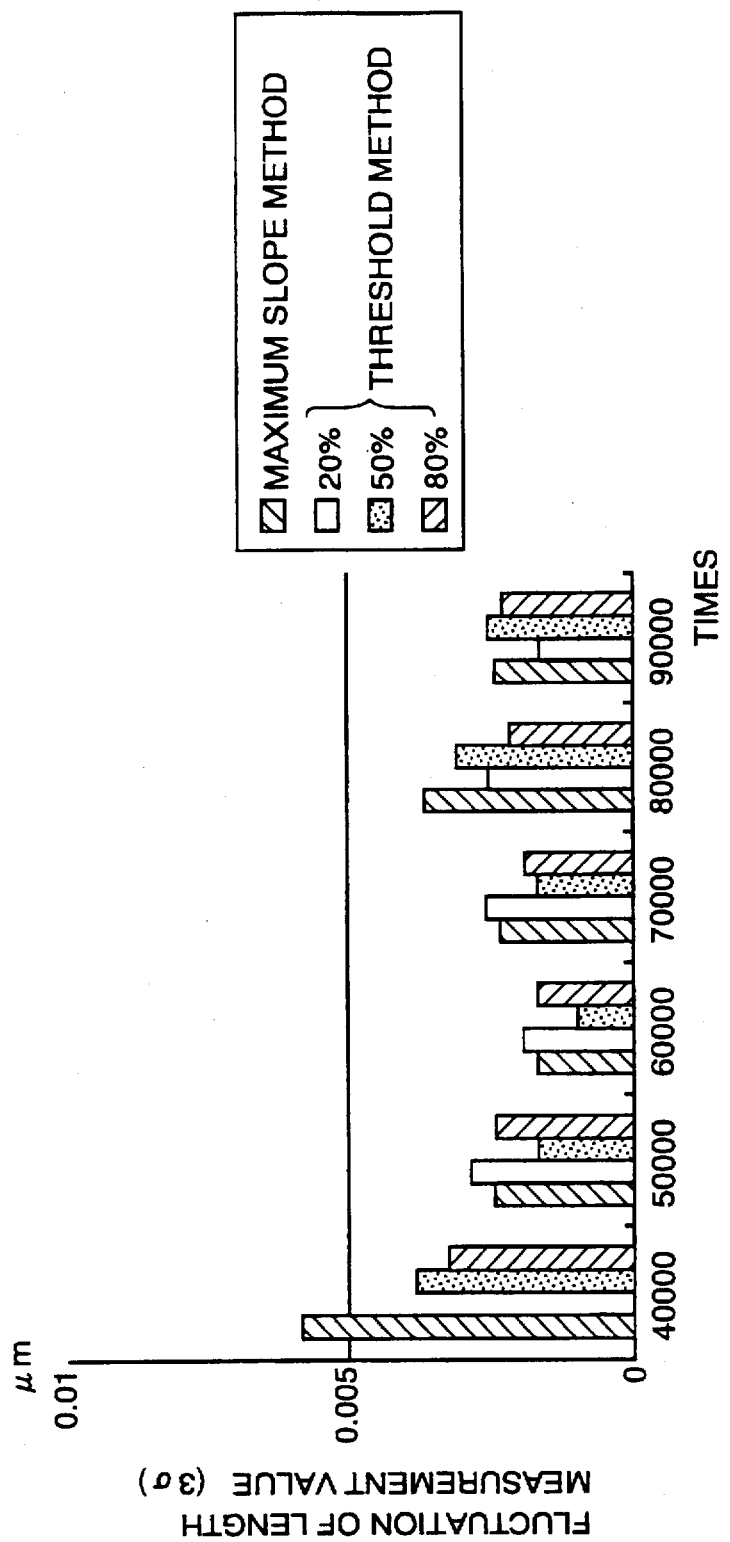
FIG. 4 is a schematic view for showing a relationship between fluctuation of the length measurement value and magnification.
Figure 5:
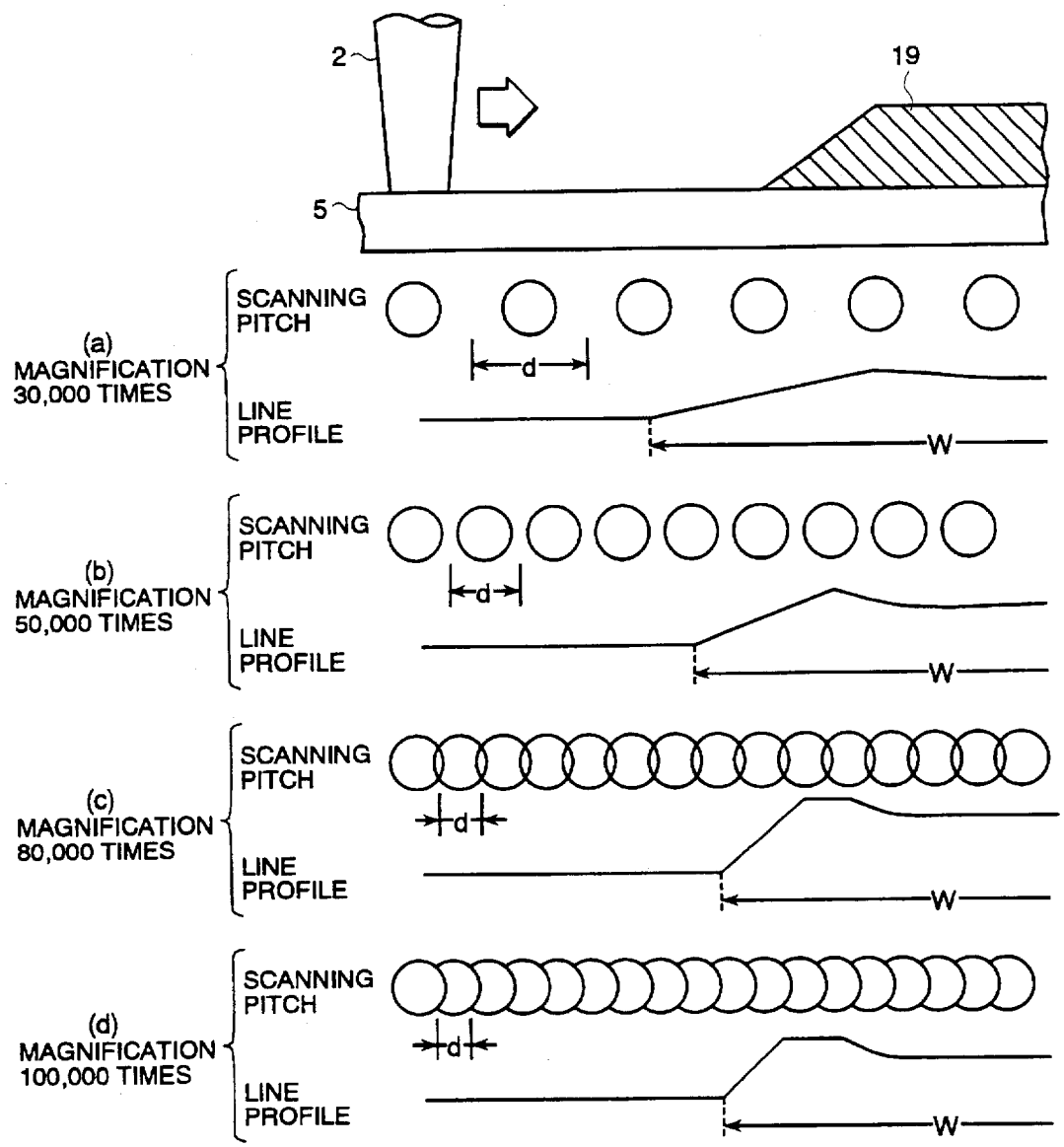
FIG. 5 is a schematic view for explaining a mechanism of magnification dependence of the dimension measured value.
Figure 9A:
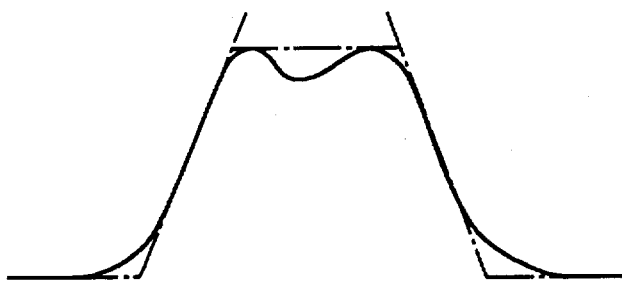
FIG. 9A is an explanatory view for explaining the maximum slope method.
Figure 9B:
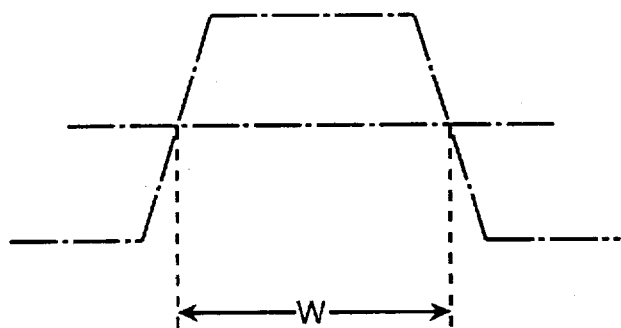
FIG. 9B is an explanatory view for measuring the pattern dimension based on the maximum slope method combined with the threshold value method.

FIG. 9 is an explanatory illustration showing the fourth embodiment. In this embodiment, as shown in FIG. 9(a), by drawing a tangent line at the maximum inclination in the slope portion of the line profile and linearly approximating the upper edge so as to linearly approximate the over off line profile to trapezoidal shape. Subsequently, as shown in FIG. 7(b), the pattern dimension W is derived in threshold method with the threshold value of 50%. It is clear from FIG. 5(a) that the measured value obtained in this method reflects the actual dimension.

Figure 10A:
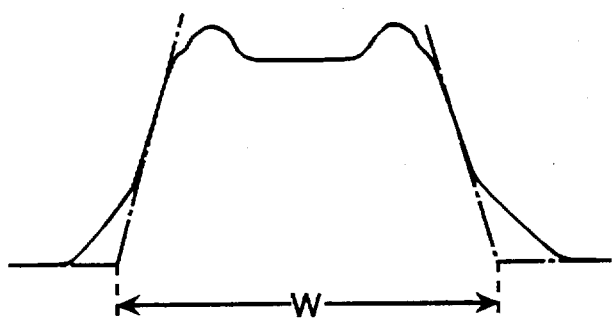
FIG. 10A is an explanatory view for measuring the pattern dimension in the high magnification based on the maximum slope method.
Figure 10B:
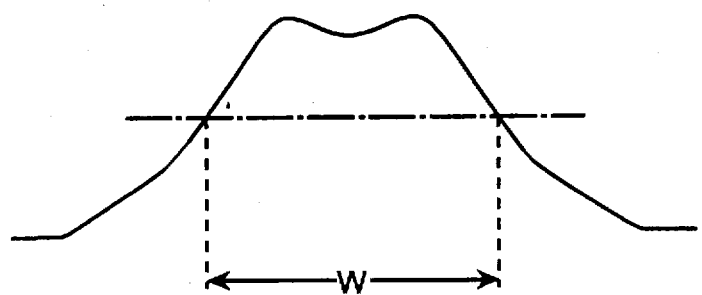
FIG. 10B is an explanatory view for measuring the pattern dimension in the low magnification based on the threshold value method.

FIG. 10 is an explanatory illustration of the fifth embodiment. In this embodiment, in length measurement at low magnification, the method is automatically switched from the maximum slope method or the linear approximation method to the threshold method.

Now, it is assumed that the maximum slope method is set as length measuring method in the length measuring SEM. As shown in FIG. 10(a), upon length measurement at high magnification, the pattern dimension W is measured in the maximum slope method as set. When the magnification is changed into low magnification in certain reason, the rounding of the waveform of the line profile becomes greater. In such case, greater error should be caused if length measurement is performed in the maximum slope method according to setting. Therefore, in the shown embodiment, when the measuring method is set to the maximum slope method or the linear approximation method, the measurement method is automatically switched to the threshold method with the threshold value 50% which method has small magnification dependence of the length measurement value.

Hereinabove, discussion has been given in terms of the length measuring SEM employing the electron beam, as the probe. However, the probe may be an optical beam (laser scanning microscope), a focused ion beam (FIB), or a mechanical probe (scanning type atomic force microscope and so forth. While an example of one probe, one pixel has been discussed hereinabove, the present invention is applicable for multiple probes or multiple pixels.

According to the present invention, magnification dependence of the length measurement value at low magnification region can be reduced and thus a precision in length measurement can be improved.

We claim:

1. A pattern dimension measuring method comprising the steps of scanning a sample at a predetermined scanning pitch by a probe, forming a sample image using a scanning signal obtained from the sample, scanning a predetermined portion of a pattern to be measured in a sample image by said probe, and measuring a dimension of said predetermined portion by processing obtained scanning signal according to a predetermined algorithm, wherein said scanning pitch is varied between upon formation of sample image and upon measurement of pattern dimension.

2. A pattern dimension measuring method as defined claim 1, wherein said probe is an electron beam.

3. A pattern dimension measuring method comprising the steps of scanning a sample at a predetermined scanning pitch by a probe, forming a sample image using a scanning signal obtained from the sample, scanning a predetermined portion of a pattern to be measured in a sample image by said probe, and deriving a dimension of said predetermined portion by processing obtained scanning signal in a threshold method, wherein a threshold value is set at a level of about 50% at a low magnification region.

4. A pattern dimension measuring method as defined claim 3, wherein said probe is an electron beam.

5. A pattern dimension measuring method comprising the steps of scanning a sample at a predetermined scanning pitch by a probe, forming a sample image using a scanning signal obtained from the sample, scanning a predetermined portion of a pattern to be measured in a sample image by said probe, and deriving a dimension of said predetermined portion by processing obtained scanning signal in a linear approximation method or maximum slop method, wherein a length measurement value is derived as a value obtained by subtracting a predetermined value determined depending upon a measurement magnification from a dimension value obtained in the linear approximation method or the maximum slop method, at low magnification region.

6. A pattern dimension measuring method as defined claim 5, wherein said probe is an electron beam.

7. A pattern dimension measuring method comprising the steps of scanning a sample at a predetermined scanning pitch by a probe, forming a sample image using a scanning signal obtained from the sample, scanning a predetermined portion of a pattern to be measured in a sample image by said probe, and deriving a dimension of said predetermined portion by processing obtained scanning signal according to a predetermined algorithm, wherein an algorithm to derive a dimension in a threshold method after drafting a linear approximation line or a maximum slope line is used as the predetermined algorithm.

8. A pattern dimension measuring method as defined claim 7, wherein said probe is an electron beam.

9. A pattern dimension measuring method comprising the steps of scanning a sample at a predetermined scanning pitch by a probe, forming a sample image using a scanning signal obtained from the sample, scanning a predetermined portion of a pattern to be measured in a sample image by said probe, and deriving a dimension of said predetermined portion by processing obtained scanning signal according to a predetermined algorithm, wherein a length measuring algorithm is switched to a threshold method at a low magnification region.

10. A pattern measuring method as defined claim 9, wherein said probe is an electron beam.

* * * * *

UNITED STATES PATENT AND TRADEMARK OFFICE
CERTIFICATE OF CORRECTION

PATENT NO. : 5,750,990
DATED : May 12, 1998
INVENTOR(S) : Fumio MIZUNO, et al.

It is certified that error appears in the above-indentified patent and that said Letters Patent is hereby corrected as shown below:

Column 1, line 23, after "deflected" insert --from--.

Column 2, line 49, change "slop" to --slope--.

Column 2, line 61, before "hand," insert --other--.

Column 2, line 66, after "may" insert --be--.

Column 3, line 3, change "slop" to --slope--.

Column 3, line 12, after algorithm" insert --which--.

Column 3, line 27, change "slop" to --slope--.

Column 3, line 47, change "is" to --are--.

Column 4, line 11, change "slop" to --slope--.

Column 4, line 14, change "slop" to --slope--.

Column 4, line 29, change "show" to --shows--.

Column 4, line 31, change "show" to --shows--.

Column 4, line 33, change "show" to --shows--.

Column 4, line 35, change "show" to --shows--.

UNITED STATES PATENT AND TRADEMARK OFFICE
CERTIFICATE OF CORRECTION

PATENT NO. : 5,750,990
DATED : May 12, 1998
INVENTOR(S) : Fumio MIZUNO, et al.

It is certified that error appears in the above-indentified patent and that said Letters Patent is hereby corrected as shown below:

```
Column 5, line 39, change "he" to --the--.
Column 6, line 66, change "in certain reason," to --for certain reasons,--.
Column 7, line 13, after "microscope" close parenthesis.
Column 7, line 30, delete "between".
Column 7, line 45, after "defined" insert --in--.
Column 8, line 8, change "slop" to --slope--.
Column 8, line 14, change "slop" to --slope--.
Column 8, line 16, after "defined" insert --in--.
Column 8, line 30, after "defined" insert --in--.
Column 8, line 42, after "defined" insert --in--.
```

Signed and Sealed this

Eleventh Day of April, 2000

Attest:

Attesting Officer

Q. TODD DICKINSON

Director of Patents and Trademarks